US007096221B2

(12) United States Patent
Nakano

(10) Patent No.: US 7,096,221 B2
(45) Date of Patent: Aug. 22, 2006

(54) FOOD INFORMATION MANAGEMENT SYSTEM

(75) Inventor: Shigeru Nakano, Shinjuku-Ku (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 112 days.

(21) Appl. No.: 09/901,595

(22) Filed: Jul. 11, 2001

(65) Prior Publication Data

US 2002/0059175 A1 May 16, 2002

(30) Foreign Application Priority Data

Jul. 12, 2000 (JP) ............................ 2000-210848

(51) Int. Cl.
*G06F 17/30* (2006.01)
*G06F 7/06* (2006.01)
(52) U.S. Cl. ..................... 707/10; 707/104.1; 235/375; 700/215
(58) Field of Classification Search ................ 707/1, 707/10, 104.1; 705/15, 22, 28; 700/213, 700/215; 283/80, 83; 235/375, 385; 40/637
See application file for complete search history.

(56) References Cited

U.S. PATENT DOCUMENTS

| | | | | |
|---|---|---|---|---|
| 4,960,983 A | * | 10/1990 | Inoue | 235/449 |
| 5,331,575 A | * | 7/1994 | Koether et al. | 700/300 |
| 5,478,990 A | * | 12/1995 | Montanari et al. | 235/375 |
| 5,640,002 A | * | 6/1997 | Ruppert et al. | 235/462.46 |
| 5,832,446 A | * | 11/1998 | Neuhaus | 705/1 |
| 6,283,914 B1 | * | 9/2001 | Mansfield et al. | 600/300 |
| 6,317,648 B1 | * | 11/2001 | Sleep et al. | 700/216 |
| 6,651,053 B1 | * | 11/2003 | Rothschild | 707/3 |
| 6,676,014 B1 | * | 1/2004 | Catan | 235/375 |

FOREIGN PATENT DOCUMENTS

| | | |
|---|---|---|
| EP | 0 965 795 | 12/1999 |
| GB | 2313940 | * 10/1997 |
| GB | 2 313 940 | 12/1997 |
| WO | 95/07007 | 3/1995 |
| WO | 00/45302 | 8/2000 |
| WO | 00/49838 | 8/2000 |

OTHER PUBLICATIONS

"Electrolux Previews Internet Refrigerator", Allnetdevices.com. News Archive, online. Feb. 12, 1999.*

(Continued)

*Primary Examiner*—Jack M. Choules
(74) *Attorney, Agent, or Firm*—Oliff & Berridge, PLC

(57) ABSTRACT

A food information management system includes a food database (11) containing food cooking conditions for cooking foods, and nutritive ingredients, energy-producing values and weight of foods, and information storage mediums (20, 20a). Each information storage medium is attached to a food package (21a) containing a processed food (21) and storing food information including food ID information specifying a food. When cooling the processed food (21), the food ID information stored in the food information storage medium (20, 20a) is read by a read means. Food information about a food specified by the food ID information is retrieved from the food database (11), an output means receives the food information, and a display means displays the food information.

8 Claims, 3 Drawing Sheets

OTHER PUBLICATIONS

"Synergy A Source Tagging Council Publication" Spring 2000, Issue 13, pp. 1-8, www.synergy-stc.com/pdf/nl13eng.pdf.*

Kaye, Joseph, "Counter Intelligence White Paper," Jun. 1999, Version 1.3, www.media.mit.edu/pia/Pubs/ci13/ci13.htm.*

Ollivier, M. M. "RFID—A Practical Solution For Problems You Didn't Even Know You Had!" Nov. 14, 1996, The Istitution of Electrical Engineers, IEE Cholloquium on Wireless Technology (Digest No. 1996/199, pp. 3/1-3/6.*

Want et al. "Bridging Physical and Virtual Worlds with Electronic Tags." 1999, Proceekings of the SIGCHI conference on Human factors in computing systems: the CHI is the limit. pp. 370-377.*

"Electrolux Previews Internet Refrigerator." Allnetdevices.com. News Archive, online. Feb. 12, 1999. www.allnetdevices.com.

"Oven, refrigerator—meet the Internet," Techserver, News Archive, online. Oct. 1, 1998. www.techserver.com.

* cited by examiner

FOOD INFORMATION MANAGEMENT SYSTEM

BACKGROUND OF THE INVENTION

1. Field of the Invention

The present invention relates to a food information management system for managing food information including cooking information. More specifically, the present invention relates to an food information management system for the automatic and intelligent cooking of processed foods using electric cooking utensils including microwave cookers and electric ovens or for the selective use of general foods.

The term "intelligent cooking" signifies the confirmation of various pieces of information about processed foods, such as nutritive ingredients, energy-producing value, weight, cooling method and cooling time, and the provision of managing means.

2. Description of the Related Art

The requirement of the food market for high-degree information about foods and processed foods has advanced progressively in recent years and the capacity of an information indicating part of a package has become insufficient for indicating a large amount of such high-degree information. Such a problem is due to the following condition of social background.

(1) The quality and grade of processed foods have been progressively enhanced with the expansion of the processed food market and it is desired that the types and qualities of processed foods can be clearly understood.

(2) An advanced in medical technology relating to adult diseases requires a diet and dietary cures, and information necessary for a diet and dietary cures.

(3) Aging society with an increasing number of aged people requires easily readable indication.

(4) It is impossible to indicate precautious information in a limited space on packages of foods.

Information necessary for the automation of cooking and nourishment management has not been unified and effective interfaces for information exchange have not been available.

The followings are concrete problems residing in information indication on conventional packages.

(1) When a person cooks a processed food, such as a frozen food or a chilled dish, by an electric cooking device, the person needs to read visually instructions specifying a heating method and heating time indicated on the package of the processed food and to set the electric cooking device for cooking. However, since only a small area is available on the package for indicating the instructions, the instructions are indicated in small letters in a small area, which is difficult for a person with poor eyesight to read such small letters. Moreover, a blind person is unable to read the instructions and needs some help. When setting an electric cooking device for cooking, it is troublesome to determine a heating time selectively according to the output capacity of the electric cooking device, it is possible that the electric cooking device is set for a wrong heating time in some cases to heat the processed food excessively or insufficiently, and it is possible that a wrong heating mode is selected, for example, a range-heating mode is selected when an oven-heating mode must be selected and vice versa.

(2) Dieticians manage diet meals in hospitals. Different patients need different ways of management individually and the qualities of different diet meals cannot be confirmed when distributing the diet meals to patients. The management of diet meals in general homes is a serious problem; people need to consult a nutritive composition table and need to manage diet meals by a complicated method.

Such problems arises when letters expressing many pieces of information are printed on the packages of foods because contradictory conditions, i.e., printing many pieces of information in a limited area on a package and printing many pieces of information in letters of a size large enough to facilitate reading the information. Such difficulties in indicating information on packages of foods will be enhanced and will become more serious with the progressive increase of kinds of information and the enhancement of the quality of information and some measures must be taken to deal with such problems.

SUMMARY OF THE INVENTION

The present invention has been made in view of the foregoing problems and it is therefore an object of the present invention to provide a food information managing system capable of storing food information including information about methods of cooking processed foods in a database and of readily retrieving the food information from the database.

According to the present invention, a food information management system includes a food database kept in a food information center and storing pieces of food information classified by food identification information, information storage mediums each incorporated into a food and storing at least food ID information specifying the food, a read means capable of reading the food ID information from the information storage medium and sending the food ID information to the food information center, and an output means capable of receiving food information from the food information center; wherein the food information center retrieves food information about a food specified by food ID information given thereto by the read means and sends the same to the output means.

In the food information management system according to the present invention, the food information stored in the food database includes cooking conditions for cooking foods, and nutritive ingredients, energy-producing values and weight of foods.

In the food information management system according to the present invention, the food information stored in the food database includes nutritive ingredients, forbidden ingredients, energy-producing values and weight of foods.

In the food information management system according to the present invention, the read means and the output means are incorporated into a cooking device.

In the food information management system according to the present invention, the read means and the output means are incorporated into a refrigerator.

In the food information management system according to the present invention, a display means capable of displaying food information about a food is connected to the output means.

In the food information management system according to the present invention, the read means and the output means are linked to the food database by the Internet.

In the food information management system according to the present invention, the information storage medium is a two-dimensional bar code marked on the food.

In the food information management system according to the present invention, the information storage medium is a noncontact IC tag provided with an IC chip and placed on a food.

In the food information management system according to the present invention, the read means and the output means are included in a read/output device on the side of a consumer.

In the food information management system according to the present invention, the read/output device is provided with a refrigerating condition determining means capable of determining a refrigerating condition on the basis of the food information provided by the output means.

In the food information management system according to the present invention, the read/output device is provided with a food quality determining means capable of determining the quality of a food on the basis of food information provided by the output means.

DESCRIPTION OF THE PREFERRED EMBODIMENTS

A food information managing system in a preferred embodiment according to the present invention will be described with reference to the accompanying drawings.

Figure 1:
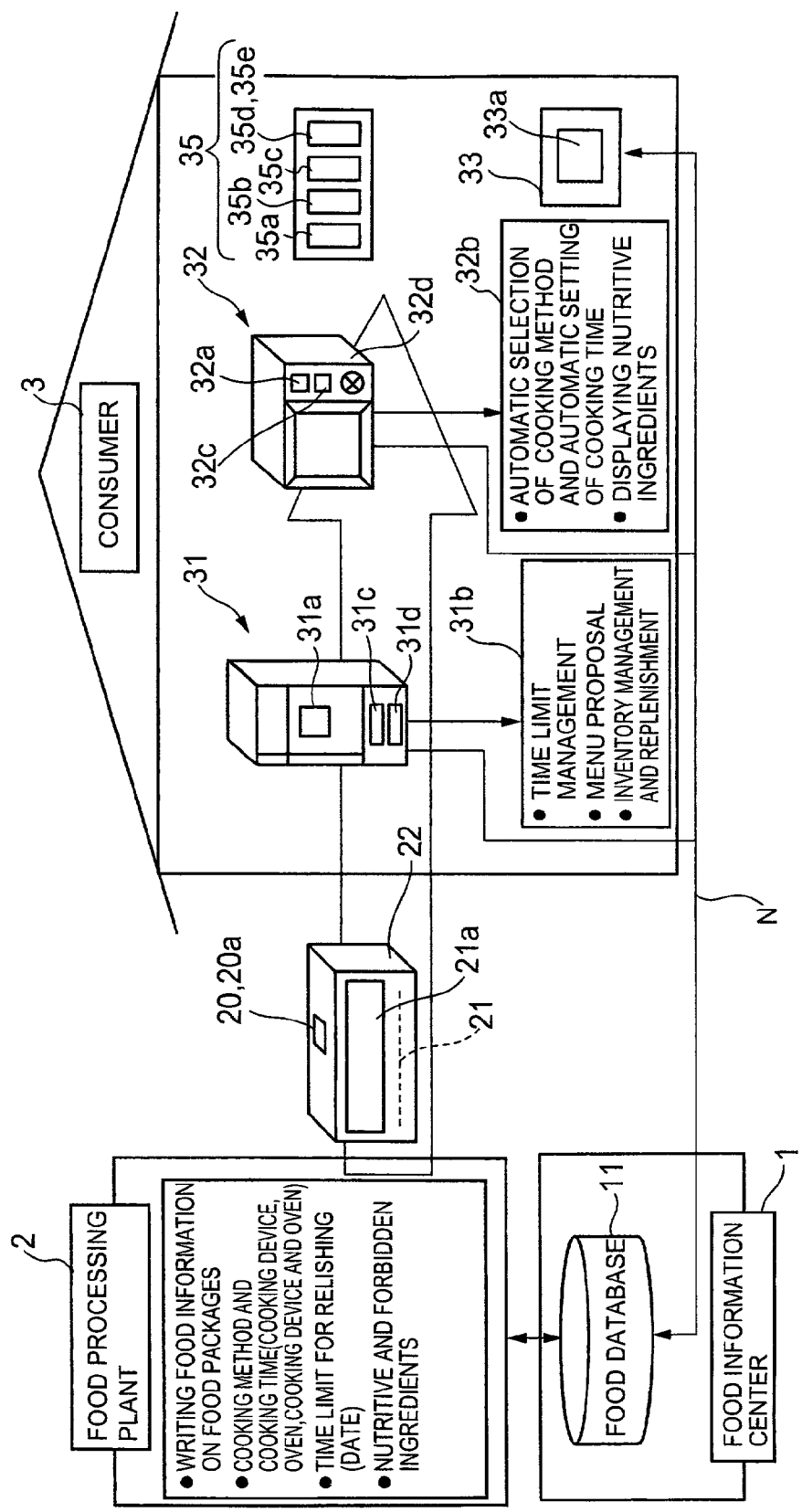
FIG. 1 is a block diagram of assistance in explaining a food information managing system in a preferred embodiment according to the present invention.

FIG. 1 is a block diagram of assistance in explaining a food information managing system in a preferred embodiment according to the present invention.

Referring to FIG. 1, a food information center 1 keeps a food database 11 storing food information including cooking information.

A food processing plant 2 produces and ships processed foods 21, and indicates food information on food packages 21a produced by packing the processed foods 21 in containers 22.

More concretely, noncontact IC tags 20 (referred to as information storage mediums, and including tags which are referred to as an RFID tag) provided with an IC chip 41 (FIG. 3) are attached to the containers 22 of food packages 21a produced by packing the processed foods 21 individually in the containers 22. The IC chip 41 stores necessary food information including food ID information specifying the processed food 21 of the food package 21a to which the noncontact IC tag 20 is attached.

The food package 21a may be provided with a label indicating information about the processed food 21. A two-dimensional bar code 20a or a one-dimensional bar code may be used instead of the noncontact IC tag 20.

Matters stored in the noncontact IC tag 20 attached to the food package 21a or indicated on a label, not shown, include kinds and nutritive ingredients of raw materials, energy-producing value (calorie), cooking information about cooking methods and cooking time, time limit for relishing, production data and the like. Data stored in the food database 11 includes at least those stored in the noncontact IC tag 20 or indicated on the label, and other relevant information specified by the food ID information specifying the processed food 21.

Principally, the relevant information is food information including cooking information. The cooking information and the food information are not entirely different from each other and the ranges thereof overlap each other. The cooking information relates principally to the cooking of the processed food, while the food information relates principally to general information about the processed food, such as the forbidden ingredients of the processed food, additives, producing conditions and the like.

The noncontact IC tag 20 attached to the food package 21a stores, in addition to information identical with that indicated on the label, additional information including at least food ID information.

A bar code or the two-dimensional bar code 20a representing information about the processed food, including the food ID information may be used instead of the noncontact IC tag 20.

The food ID information specifying the processed food 21 of the food package 21a is stored in the noncontact IC tag 20 attached to the food package 21a. The food ID information is used as a key for retrieving food information including cooking information from the food database 11 kept by the food information center 1. Although it is preferable that the food ID information stored in the noncontact IC tag 20 includes a serial number assigned to the food package 21a, one and the same ID information may be stored in the noncontact IC tags 20 attached to food packages containing foods of the same quality and produced under the same processing conditions on the same day.

Information representing the food package 21a produced by the food processing plant 2 and the food ID information are stored in the food database 11 kept by the food information center 1 and are managed by the food information center 1.

The food processing plant 2 is able to refer to the contents of the food database 11 kept by the food information center 1 whenever need arises. The food information center 1 is associated with many food processing plants and food makers for exchanging food information.

The food information center 1 provides necessary information in response to inquiries made by a refrigerator 31 and an electric cooking device, such as a microwave cooker 32, possessed by a consumer 3.

The food package 21a produced by packaging the processed food 21 in a container 22 is shipped from the food processing plant 2, is distributed by a physical distribution and is bought by the consumer 3 from a retail shop. Usually, the food package 21a containing the processed food 21 and bought by the consumer 3 is stored temporarily in the refrigerator 31.

The refrigerator 31 and the microwave cooker 32 are provided with read units 31a and 32a, display units 31b and 32b, output units 31c and 32c and controllers 31d and 32d, respectively. The read units 31a and 32a read the food ID information, send the same through the Internet N to the food database 11 and inquire of the food database 11 food information including cooking information, such as a cooking method, cooking time (method of heating by the microwave cooker and time for which the food is to be heated), nutritive ingredients and energy-producing value.

Food information corresponding to the food ID information is retrieved from the food database 11, and the food information is sent to the refrigerator 31 and the microwave cooker 32. The output units 31c and 32c of the refrigerator 31 and the microwave cooker 32 give the food information to the display units 31b and 32b, and the display units 31b and 32b display the food information.

When the two-dimensional bar code 20a represents the food information about the processed food 21 or the IC chip 41 of the noncontact IC tag 20 stores the food information, the read unit 31a, such as a bar code reader or a noncontact IC tag reader, of the refrigerator 31 reads the food information. Then controller 31d manages the time limit for relishing, proposes possible menus based on the contents of the refrigerator 31, performs inventory management, specifies deficient stock of foods and proposes foods to be purchased.

The controller 31d of the refrigerator 31 creates data for the management of the time limit and the proposal of foods to be purchased and the display unit 31c, such as a liquid crystal display, of the refrigerator 31 displays the data.

The microwave cooker 32, i.e., the consumer's electric cooking device, is provided with the read unit 32a, such as a bar code reader or a noncontact IC tag reader.

When the two-dimensional bar code 20a represents cooking information or the noncontact IC tag 20 stores cooking information, the read unit 32a of the microwave cooker 32 reads the cooking information. The microwave cooker 32 is set automatically for a cooking time. An automatic cooking operation of the microwave cooker 32 can be started simply by depressing a start button 32d.

When the two-dimensional bar code does not represent cooking information and represents only the food ID information or the noncontact IC tag 20 does not store cooking information and stores only the food ID information, the read unit 32a, such as a bar code reader or a noncontact IC tag reader, reads the food ID information and inquires of the food database 11 kept by the food information center 1, food information including cooling information.

The microwave cooker 32 is connected through the Internet N to the food database 11. The food database 11 sends food information about the processed food 21 specified by the food ID information to the output unit 32b. The output unit 32b gives the food information to the display unit 32b and the display unit 32b displays the food information. Techniques for distributing information by a combination of techniques relating to domestic, digital, electric utensils and a fast internetwork instead of the Internet have been studied. It is expected that the demonstrative experiments of those techniques are started before the year 2002 (Refer to Nippon Keizai Shinbun, May 17, 2000).

Inquiries to the food database 11 kept by the food information center 1 may be made by the microwave cooker 32 through a home server 33. The microwave cooker 32 communicates with the home server 33 by cable communications or wireless communications, and the home server 33 is connected to the food database 11 of the food information center 1 by an on-line network, such as the Internet N. Food database 11 sends food information through the home server 33 to the microwave cooker 32.

Manual inquiries can be made to the food database 11. In this case, information provided by the food database 11 may be displayed by a display unit 33a included in the home server 33.

The microwave cooker 32 can be automatically set for cooking conditions based on the cooking information of the food information or can be manually set on the basis of information displayed by the display unit 32b.

After the microwave cooker 32 has been set for desired cooking conditions, the microwave cooker 32 cooks the processed food 21. The processed food 21 contained in the food package 21a is placed on a rotary dish and is heated for a set cooking time.

The processed food 21 may be cooked by a complicated cooking method including steps of heating by microwave heating and oven-heating, and intermittent operation suitable for cooking the processed food 21 so that the cooked processed food 21 has the utmost taste and flavor by using a microwave cooker having the function of an oven instead of the microwave cooker 32 having only heating capability.

The microwave cooker 32 must be provided with the read unit 32a capable of reading food information from the two-dimensional bar code 20a or the noncontact IC tag 20 and must be capable of reading the food ID information specifying the processed food 21. The microwave cooker 32 is provided with a selector switch for setting the microwave cooker 32 for either an automatic cooking condition setting mode or a manual cooking condition setting mode. Set cooking conditions are displayed by the display unit 32b.

The read unit 32a, such as a bar code reader or a noncontact IC tag reader, is placed outside the microwave cooker 32 or on the front panel, and the food package 21a is held opposite to the read unit 32a by hand to ensure reading the food ID information. The food ID information red by the read unit 32a is used as a key to retrieve food information about the processed food 21 through the Internet N from the food database 11.

The food information management system has been described as applied to managing the cooking information included in the food information. The food information management system may be applied to the management of food information other than the cooking information.

Food information other than the cooking information is not directly related with cooking conditions; such food information includes reference data on the nutritive ingredients and forbidden ingredients of foods, the energy-producing values of foods and foods inadvisable to patients in particular conditions of diseases.

Thus the addition of information about unprocessed foods to the food database 11 will enhance the utility value of the food database 11.

The information can be retrieved from the food database 11 of the food information center 1 by the same system as the aforesaid cooking information distributing and managing system.

When necessary, information about the energy-producing value and nutritive ingredients of a processed food may be retrieved from the food database 11 by sending food ID information read by a read unit 35a included in a read/output device 35. The food information from the food database 11 may be sent to an output unit 35c of the read/output device 35, and then displayed by a display unit 35b of the read/output device 35. When the date of expiry of the time limit for relishing is approaching or the time limit for relishing has expired, the display unit 35b of the read/output device 35 displays a warning to that effect.

Food information other than the cooking information will be of some help toward food management when the nutritive ingredients and inadvisable ingredients and energy-producing values of foods are displayed by the display unit 35b of the read/output device 35. When distributing meals to patients in a hospital, the IC information in the noncontact IC tag is read by a read device 35a, such as a portable reader, and the food information from the food database 11 is sent to the output unit 35c. Then, a food quality determining means 35d determines whether or not the meals are proper to the patients on the basis of the food information from the food data base 11 and the conditions of the patients.

Thus aged persons, poor-sighted persons and normal persons are able to cook foods easily and properly.

The refrigerating condition of the refrigerator 31 may be decided by a refrigerating condition determining unit 35e which is provided in place of the food quality determining means 35*d* on the basis of information retrieved from the food database 11.

Food ID Code

Indication and recording of food ID information will be explained.

Food information including cooking information can be retrieved without any restriction through the Internet N from the food database 11. The noncontact IC tag 20 or the two-dimensional bar code 20*a* attached to the food package 21*a* of the processed food 21 includes at least food ID information. Minimum necessary information is indicated visibly on the food package 21*a* as a backup means for use in the case of system down.

The food ID information may be represented by a bar code or the two-dimensional bar code 20*a*, which can be read by the read unit 31*a*, 32*a* or 35*a*, such as a bar-code reader.

The JAN code (Japan Article Number code), i.e., one of one-dimensional bar code, is used prevalently. The JAN code represents a thirteen-digit number and is used for various purposes.

Generally, from the left to the right, the first two digits form a country code, the following five digits represent the registered number of maker, the five digits represent an article number and the last one digit forms a check code.

Numerals represented by the bars of the bar code are indicated below the bars, respectively. A country code 49 indicates Japan. Therefore, the first and the second digit of a bar code assigned to an article made in Japan are 4 and 9.

A physical distribution system uses an ITF code formed by putting a one- or two-digit distribution code in front of the JAN code. Therefore, if the JAN code is used, any other information needed by the system cannot be indicated and an article number is used in substitution for the ID code.

Figure 2:
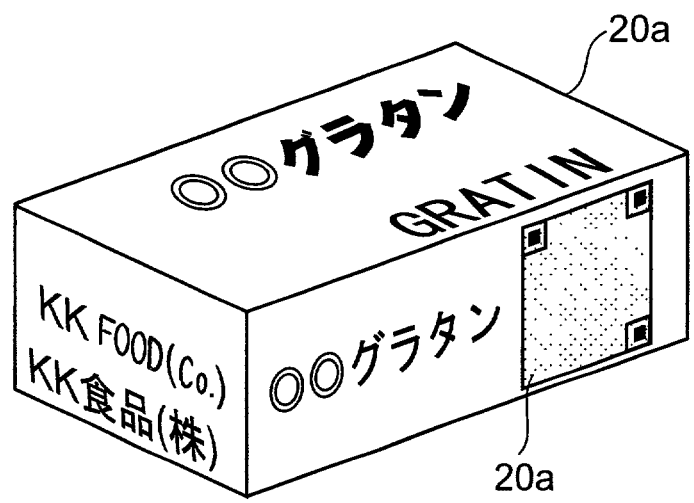
FIG. 2 is a perspectively view showing a two-dimensional bar code marked on a food package.

FIG. 2 shows a food package 21*a* provided with a two-dimensional bar code 20*a*.

The two-dimensional bar code 20*a* is marked in a plane. The QR Code, the Code 49 and Maxi Code are two-dimensional bar codes. The two-dimensional bar code is capable of representing about 400-digit alphanumeric characters. The two-dimensional barcode 20*a* is capable of representing a considerably large amount of information in addition to the food ID information.

However, the two-dimensional bar code 20*a* is only for reading and any code cannot be added to the two-dimensional bar code 20*a* in the stage of distribution and retail after shipment.

The two-dimensional bar code 20*a* shown in FIG. 2 is a QR code.

Figure 3:
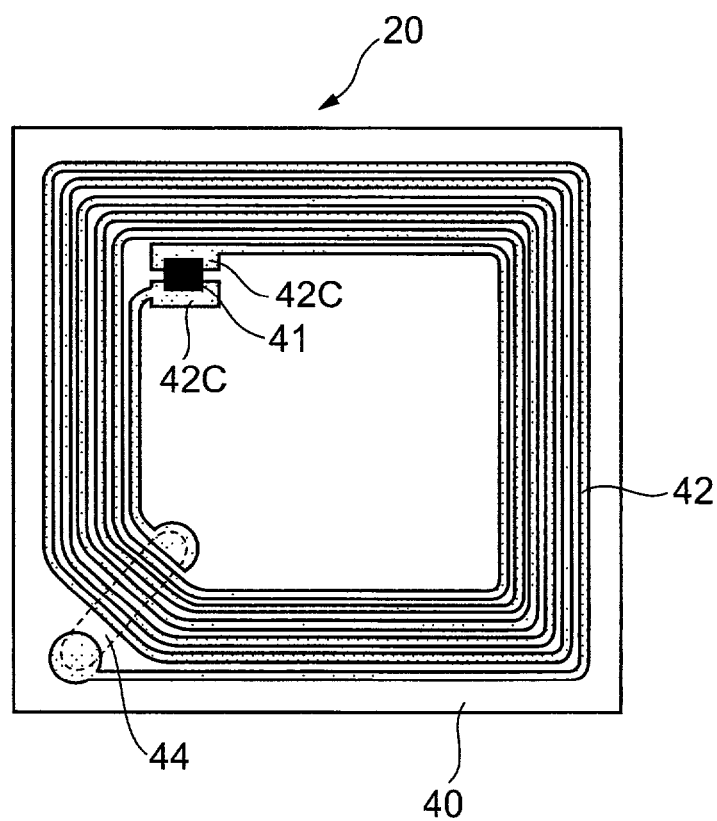
FIG. 3 is a plan view of a noncontact IC tag.

An IC chip 41 shown in FIG. 3 has a recording capacity of 1024 bits, is capable of recording 128 characters and is applicable to an ordinary label required to recording a minimum necessary information.

An IC chip having a recording capacity of several kilobits is capable of representing an amount of information greater than that of information that can be represented by the two-dimensional bar code 20*a*. Additional information can be written to the IC chip and information stored in the IC chip can be erased. Thus it is preferable to use a noncontact IC tag 20 provided with a writable and erasable IC chip 41 when the indicated price of an article is changed at the cashier or when the date of delivery is entered into the noncontact IC tag 20.

Thus the food information management system of the present invention uses the two-dimensional bar code 20*a* or a noncontact IC tag 20 provided with a ROM (read-only memory) when the information is not changed after shipment. The food information management system uses a noncontact IC tag 20 provided with a writable IC chip 41 when additional information is added or the initial information is changed in the stage of distribution.

FIG. 3 shows the noncontact IC tag 20.

The noncontact IC tag 20 includes a plastic base 40, a coil pattern 42 and an IC chip 41. The coil pattern 42 and the IC chip 41 constitute a resonance circuit that sends out a signal upon the reception of a radiowave of a predetermined frequency. A jumper line 44 formed on the back surface of the base 40 is connected to the coil pattern 42 and a terminal 42*c* connected to the jumper line 44 is connected to a bump formed on the back surface of the IC chip 41. The IC chip 41 is provided with a built-in capacitor.

The coil pattern 42 shown in FIG. 3 is formed by bonding a metal foil, such as an aluminum foil or a copper foil to a surface of the plastic base 40 and etching the metal foil.

A microwave of 125 kHz, 13.56 MHz, 2.45 GHz or 5.8 GHz is used for communication between the read units 31*a*, 32*a* and 35*a*, and the noncontact IC tag 20.

The noncontact IC tag 20 is not limited to such as shown in FIG. 3 but may be a noncontact IC tag provided with simpler pattern. The noncontact IC tag may be, for example, a noncontact IC tag provided with a printed antenna pattern having the shape of two wings and printed on a base, and an IC chip bonded to the base with its terminals connected to the antenna pattern. The antenna pattern can be formed on the food package 21*a* by printing the same directly on the food package 21*a* in a black ink containing carbon or a conductive ink containing aluminum paste.

The noncontact IC tag 20 may be formed either on the inner or the outer surface of the food package 21*a*.

Bar Code Reader (Read Means)

A QR code scanner, i.e., a bar code reader, is capable of instantly reading a large amount of data represented by a two-dimensional bar code 20*a* regardless of the directional position of the two-dimensional bar code 20*a*. Even if the food package 21*a* is deformed or slightly soiled the QR code scanner is able to read the two-dimensional bar code 20*a* from a position at a distance on the order of 1 m. The QR code scanner is available in a portable type or a stationary laser-scanning type. The QR code scanner can be placed in the microwave cooker 32.

Noncontact IC Tag Reader (Read Means)

A noncontact IC tag reader, also called a scanner, sends a radiowave of a predetermined frequency to the noncontact IC tab 20 and detects a response wave from the noncontact IC tag 20. Since the refrigerator 31 stores many foods of many kinds, noncontact IC tags attached to those different foods must store food ID information different from each other.

When the refrigerator 31 stores many processed foods and the many noncontact IC tags 20 respond simultaneously to the radiowave applied thereto, data collision may occur. Various communication methods of sequentially communicating with a plurality of noncontact IC tags without causing data collision, including a communication method disclosed in JP-A No. Hei 8-36623, have been proposed.

Food Information Including Cooking Information

Pieces of the food information will be specifically described. Generally, the following pieces of information are necessary.

The food Information Includes 1-1: processed food maker and its nationality, 1-2: designation of the processed food, 1-3: time and data of production, time limit for consumption and time limit for relishing, 1-4: ingredients (materials, additives, preservatives and such), 1-5: net weight, 1-6: cooking method and cooking time, 1-7: nutritive ingredients and their contents, 1-8: energy-producing value (calorie) and 1-9: stocking temperature range.

The food information including the cooking information is needed not only in the stages of manufacture by the makers and consumption by consumers but also in the stages of distribution and disposal.

Figure 4:
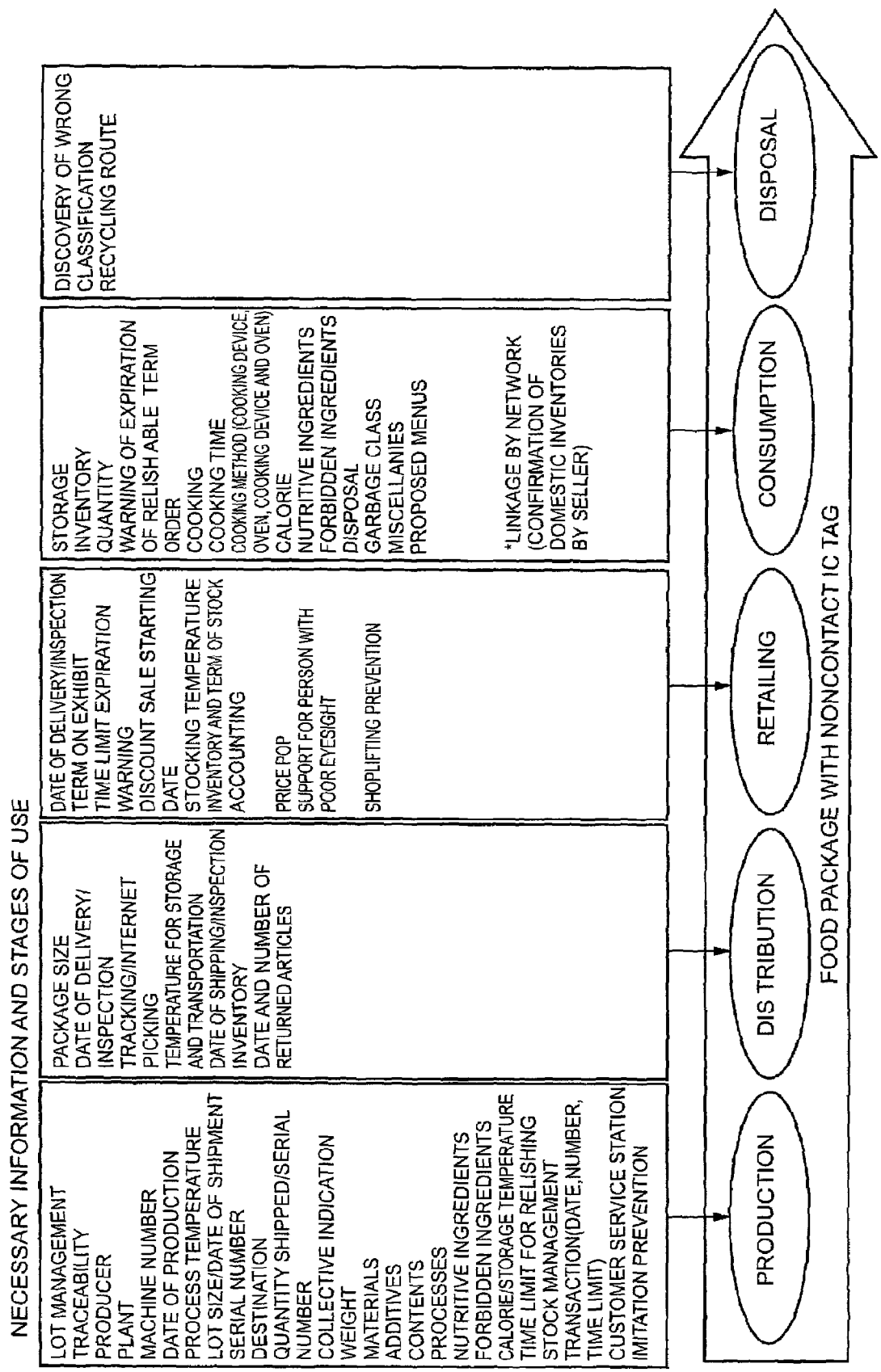
FIG. 4 is a table of pieces of food information needed at stages including a production stage, a distribution stage, a retail stage, a consumption stage and a disposal stage.

FIG. 4 is a table of pieces of food information needed at stages including a production stage, a distribution stage, a retail stage, a consumption stage and a disposal stage.

The production stage needs, in addition to the foregoing information, pieces of information about lot, producing conditions, date of shipment and destination.

The distribution Stage Needs 2-1: date of delivery and inspection, 2-2: tracking information, 2-3: temperatures during storing and transportation and 2-4: date of inspection and stock.

The retail stage needs, in addition to the information needed at the distribution stage, 3-1: retail price, 3-2: assistive information for persons with poor eyesight, such as audio information that is provided when a portable telephone is directed toward the food package and 3-3: shoplifting preventing means. Since the noncontact IC tag 20 sends out an electromagnetic wave of a fixed frequency, shoplifting can be prevented by detecting the electromagnetic wave sent out by the food package by a gate, not shown.

It is preferable to provide the consumption stage with information about 4-1: disposal, 4-2: dust classification and 4-3: proposed menus in addition to the aforesaid information about keeping, stocking, amount of food, energy-producing value (calorie), nutritive ingredients, forbidden ingredients, time limit and cooking conditions.

It is preferable the information for the disposal stage includes information about 5-1: means for detecting wrong classification and 5-2: recycling route.

As apparent from the foregoing description, the food information management system of the present invention is capable of retrieving the necessary food information without any restriction from the food database 11 of the food information center 1 by using the food ID information recorded on the noncontact IC tag 20 attached to the food package 21a or the two-dimensional barcode 20a formed on the food package 21a. Thus, even an area for indicating food information, is limited on the food package 21a, cooking conditions for cooking foods and various necessary pieces of food information can be obtained from the food database 11 only by reading the food ID information from the food package 21a by the read unit.

What is claimed is:

1. A food information management system, comprising:
a food processing plant for producing and shipping food in food packages, each of the food packages comprising an RFID tag storing at least food identification information relating to the food in the food package;
a food information center comprising a food database, the food database comprising food information including cooking information classified by the food identification information;
read means for reading the food identification information provided on the RFID tags and for sending the food identification information to the food information center;
output means for receiving the food information from the food information center; and
display means capable of displaying the food information; wherein:
when the read means sends the food identification information to the food information center, the food information center retrieves the food information associated with the food identification information, and sends the food information to the output means;
the read means and the output means are provided in a cooking device, and the read means and the output means interact with the food information center remotely over a network; and
the display means is connected to the output means.

2. The food information management system according to claim 1, wherein the food information comprises cooking conditions for cooking the food, nutritive ingredients in the food, energy-producing values of the food and a weight of the food.

3. The food information management system according to claim 1, wherein the food information comprises nutritive ingredients in the food, forbidden ingredients in the food, energy-producing values of the food and a weight of the food.

4. The food information management system according to claim 1, wherein the network is the Internet.

5. A food information management system, comprising:
a food processing plant for producing and shipping food in food packages, each of the food packages comprising an RFID tag storing at least food identification information relating to the food in the food package;
a food information center comprising a food database, the food database comprising food information including cooking information classified by the food identification information;
read means for reading the food identification information provided on the RFID tags and for sending the food identification information to the food information center;
output means for receiving the food information from the food information center; and
display means capable of displaying the food information; wherein:
when the read means sends the food identification information to the food information center, the food information center retrieves the food information associated with the food identification information, and sends the food information to the output means;
the read means and the output means are provided in a refrigerator, and the read means and the output means interact with the food information center remotely over a network; and
the display means is connected to the output means.

6. The food information management system according to claim 5, wherein the food information comprises cooking conditions for cooking the food, nutritive ingredients in the food, energy-producing values of the food and a weight of the food.

7. The food information management system according to claim 5, wherein the food information comprises nutritive ingredients in the food, forbidden ingredients in the food, energy-producing values of the food and a weight of the food.

8. The food information management system according to claim 5, wherein the network is the Internet.

* * * * *